US008235055B2

(12) United States Patent
Mintchev et al.

(10) Patent No.: US 8,235,055 B2
(45) Date of Patent: Aug. 7, 2012

(54) MAGNETIC LEVITATION OF INTRALUMINAL MICROELECTRONIC CAPSULE

(75) Inventors: Martin P. Mintchev, Calgary (CA); Billy T. Wu, Calgary (CA)

(73) Assignee: UTI Limited Partnership, Calgary (CA)

( * ) Notice: Subject to any disclaimer, the term of this patent is extended or adjusted under 35 U.S.C. 154(b) by 1976 days.

(21) Appl. No.: 11/330,044

(22) Filed: Jan. 11, 2006

(65) Prior Publication Data

US 2006/0152309 A1    Jul. 13, 2006

Related U.S. Application Data

(60) Provisional application No. 60/643,392, filed on Jan. 11, 2005, provisional application No. 60/719,887, filed on Sep. 23, 2005.

(51) Int. Cl.
*A61B 19/00* (2006.01)
(52) U.S. Cl. ............................................... 128/899
(58) Field of Classification Search ............... 128/899; 600/424, 587, 593; 604/95.01
See application file for complete search history.

(56) References Cited

U.S. PATENT DOCUMENTS

| | | | |
|---|---|---|---|
| 4,632,119 A | 12/1986 | Reichstein |
| 4,748,562 A | 5/1988 | Miller |
| 4,981,470 A | 1/1991 | Bombeck |
| 5,109,870 A | 5/1992 | Silny |
| 5,297,437 A | 3/1994 | Schneider |
| 5,411,477 A | 5/1995 | Saab |
| 5,438,985 A | 8/1995 | Essen-Moller |
| 5,604,531 A | 2/1997 | Iddan |
| 5,681,260 A | 10/1997 | Ueda |
| 5,688,776 A | 11/1997 | Bauer |
| 5,792,048 A | 8/1998 | Schaefer |
| 5,833,625 A | 11/1998 | Essen-Moller |
| 6,153,222 A | 11/2000 | Becher |
| 6,233,476 B1 | 5/2001 | Strommer |
| 6,285,897 B1 | 9/2001 | Kilcoyne |
| 6,374,670 B1 | 4/2002 | Spelman |
| 6,475,145 B1 | 11/2002 | Baylor |
| 6,505,654 B1 | 1/2003 | Andersen |

(Continued)

FOREIGN PATENT DOCUMENTS

WO    2004041068    5/2004

OTHER PUBLICATIONS

Kallay, N., et al., "Inner Layer Capacitor at the Solid/Liquid Interface," Croatica Chemica Acta, May 26, 2003, pp. 243-249, vol. 77, Croatia.

(Continued)

*Primary Examiner* — Max Hindenburg
*Assistant Examiner* — Jonathan M Foreman
(74) *Attorney, Agent, or Firm* — Fulbright & Jaworski

(57) ABSTRACT

A method and apparatus for magnetically levitating and further steering of an intraluminal device, such as a swallowable microelectronic capsule, for monitoring bodily functions is provided. The method comprises diamagnetically-stabilized levitation, followed by dynamic modification of the external magnetic field producing the said levitation, so that the levitating intraluminal device can be steered in desired direction. The said intraluminal device contains appropriate sensors and reports in real time the forces and pressures exerted on it, as well as its position, so that the levitation and the steering can be dynamically adjusted using appropriate dynamic control of external magnetic devices such as solenoids.

7 Claims, 7 Drawing Sheets

U.S. PATENT DOCUMENTS

| | | | |
|---|---|---|---|
| 6,535,764 B2 | 3/2003 | Imran | |
| 6,635,834 B1 | 10/2003 | Wenner | |
| 6,689,056 B1 | 2/2004 | Kilcoyne | |
| 6,776,165 B2 | 8/2004 | Jin | |
| 6,799,462 B1 | 10/2004 | Berstis | |
| 7,061,523 B2 | 6/2006 | Fujita | |
| 7,104,952 B2 | 9/2006 | Iddan et al. | |
| 2002/0099310 A1 | 7/2002 | Kimchy | |
| 2002/0187721 A1 | 12/2002 | Chung | |
| 2003/0020810 A1 | 1/2003 | Takizawa | |
| 2003/0023150 A1* | 1/2003 | Yokoi et al. | 600/300 |
| 2003/0114742 A1* | 6/2003 | Lewkowicz et al. | 600/407 |
| 2003/0125788 A1 | 7/2003 | Long | |
| 2004/0192582 A1 | 9/2004 | Burnett | |
| 2004/0199054 A1 | 10/2004 | Wakefield | |
| 2005/0043634 A1 | 2/2005 | Yokoi | |
| 2005/0054902 A1 | 3/2005 | Konno | |
| 2005/0183733 A1 | 8/2005 | Kawano | |
| 2005/0186244 A1 | 8/2005 | Hunter | |
| 2005/0187140 A1 | 8/2005 | Hunter | |
| 2005/0196421 A1 | 9/2005 | Hunter | |
| 2005/0208095 A1 | 9/2005 | Hunter | |
| 2005/0216231 A1 | 9/2005 | Aoki | |
| 2005/0250991 A1 | 11/2005 | Mizuno | |
| 2005/0256372 A1 | 11/2005 | Yokoi | |
| 2005/0266074 A1 | 12/2005 | Zilberstein | |
| 2005/0272973 A1 | 12/2005 | Kawano | |
| 2005/0288557 A1 | 12/2005 | Yokoi | |
| 2006/0030752 A1 | 2/2006 | Orihara | |
| 2006/0063974 A1 | 3/2006 | Uchiyama | |
| 2006/0116564 A1 | 6/2006 | Mintchev | |
| 2006/0152309 A1 | 7/2006 | Mintchev | |
| 2006/0162452 A1 | 7/2006 | Moser | |
| 2006/0169294 A1 | 8/2006 | Kaler | |
| 2006/0178557 A1 | 8/2006 | Mintchev | |
| 2006/0209185 A1 | 9/2006 | Yokoi | |
| 2006/0229592 A1 | 10/2006 | Yokoi | |
| 2006/0231110 A1 | 10/2006 | Mintchev | |
| 2006/0238614 A1 | 10/2006 | Konno | |
| 2006/0252986 A1 | 11/2006 | Akagi | |
| 2006/0258901 A1 | 11/2006 | Fujimori | |
| 2006/0264083 A1 | 11/2006 | Fujimori | |
| 2006/0264704 A1 | 11/2006 | Fujimori | |
| 2006/0264709 A1 | 11/2006 | Fujimori | |
| 2007/0010702 A1 | 1/2007 | Wang | |
| 2007/0030344 A1 | 2/2007 | Miyamoto | |
| 2007/0032698 A1 | 2/2007 | Uchimura | |
| 2007/0032699 A1 | 2/2007 | Segawa | |

OTHER PUBLICATIONS

Kern, M.K., "Kinematic and Dynamic Characteristics of Solid . . . etc." [abst], Annals of Otol., Rhinol. and Laryngol., Sep. 1996, pp. 716-723, vol. 105, Annals Pub. Co., USA.

Ku, D.N., et al., "A Kinematic Study of the Oropharyngeal Swallowing . . . etc.", Annals of Biomedical Engineering, Nov. 1990, pp. 655-669, vol. 18, No. 6, Springer, Netherlands.

Kubler, C., "Endoscopic Robots," Lecture Notes in Computer Science, Feb. 2000, pp. 949-955, vol. 1935.

Kwan, K.Y., et al., "High-Pressure Balloon Catheter . . . etc." [abst], 9th Int'l Conf on Electronics, Circuits and Systems, Sep. 2002, pp. 1211-1214, vol. 3, Dubrovnik, Croatia.

Lauto, A., et al, "Self-Expandable Chitosan Stent: Design and Preparation," Biomaterials, Jul. 2001, pp. 1869-1874, vol. 22.

Layne, K.A., et al., "Using the Fleming Index of Dysphagia to Establish Prevalence," Dysphagia, Mar. 1989, pp. 39-42, vol. 4(1).

Lee, W.F., et al., "Electrical Modeling of MEMS Sensor for Integrated Accelerometer Applications," Electron Devices Meeting, Jun. 1999, pp. 88-91, IEEE Hong Kong, Hong Kong.

Lewis, B.S., "The Utility of Capsule Endoscopy in Obscure Gastrointestinal Bleeding," Techniques in Gastrointestinal Endoscopy, Jul. 2003, pp. 115-120, vol. 5(3).

Lindgren, S., et al., "Prevalence of Swallowing Complaints and Clinical Findings Among . . . etc.," Dysphagia, Dec. 1991, pp. 187-189, vol. 6(4).

Locke, G.R, et al., "Prevalence and Clinical Spectrum of Gastroesophageal Reflux . . . etc.," Gastroenterology, May 1997, pp. 1448-1456, vol. 112.

Lynch, J.P., et al., "Design of a Piezoresistive MEMS-Based Accelerometer . . . etc.," Journal of Aerospace Engineering, Jul. 2003, pp. 108-114, vol. 6, Issue 3, ASCE, USA.

Marsden, G., "Levitation! Float Objects in a . . . ," Sep. 2003, <http://www.arttec.net/Press/N&V/Levitation.pdf> [retrieved Jan. 17, 2007].

Menciassi, A., et al., "Shape Memory Alloy Clamping . . . etc.," Journal of Micromechanics and Microengineering, Nov. 2005, pp. 2045-2055, vol. 15(11).

Meng, M., et al., "Wireless Robotic Capsule Endoscopy . . . etc.," IEEE Intelligent Control and Automation 5th World Congress, Jun. 2004, pp. 5561-5565, Hangzhou, China.

Mintchev, M.P., U.S. Appl. No. 60/618,955, filed Oct. 14, 2004.
Mintchev, M.P., U.S. Appl. No. 60/636,474, filed Dec. 15, 2004.
Mintchev, M.P., U.S. Appl. No. 60/643,392, filed Jan. 11, 2005.
Mintchev, M.P., U.S. Appl. No. 60/650,278, filed Feb. 4, 2005.
Mintchev, M.P., U.S. Appl. No. 60/664,633, filed Mar. 24, 2005.

Morgan, P.N., et al, "Resistive Homogeneous MRI Magnet Design by Matrix Subset Selection," Magnetic Resonance in Medicine, Jun. 1999, pp. 1221-1229, vol. 41.

Nelson, C., et al., "National Ambulatory Medical Care Survey: 1993 summary," [abst] Vital Health Stat. 13, Apr. 1998, pp. 1-99.

Olympus Inc., "Development of Capsule . . . ," Nov. 30, 2004, <http://www.olympus-global.com/en/news/2004b/nr041130capsle.cfm?ote=1&nr=1> [retrieved Jan. 17, 2007].

Pandolfino, J.E., et al., "AGA Technical Review on the Clinical Use of Esophageal Manometry," Gastroenterology, Jan. 2005, pp. 209-224, vol. 128.

Pandolfino, J.E., et al., "Ambulatory Esophageal pH Monitoring Using . . . etc.," The American Journal of Gastroenterology, Apr. 2003, pp. 740-749, vol. 98, Chicago, USA.

Pandolfino, J.E., et al, "American Gastroenterological Association Medical Position Statement . . . etc.," Gastroenterology, Jan. 2005, pp. 207-208, vol. 128.

Pozar, D.M., "Microstrip Antennas," Proceedings of the IEEE, Jan. 1992, pp. 79-91, vol. 80.

"Radiography—Upper GI Tract," Radiological Society of North America, May 2003, <http://www.radiologyinfo.org>, Chicago, USA.

Ren, J., et al., "Determinants of Intrabolus Pressure . . . etc.," Am. J. Physiol. Gastrointest. Liver Phys., Mar. 1993, pp. 407-413, vol. 264, American Physiological Society, USA.

Rhee, E.J., et al., "The Position Control of a Capsule . . . etc.," Journal of Magnetism and Magnetic Materials, Nov. 2002, pp. 350-352, vol. 252.

Ruan, C., et al., "A Wireless pH Sensor Based on the Use of Salt . . . etc.," Sensors and Actuators B: Chemical, Nov. 2003, pp. 61-69, vol. 96.

Sadiku, M., et al., "Magnetic Levitation," IEEE Potentials, Mar. 2006, pp. 41-42, vol. 25(2).

Sendoh, M., et al., "Fabrication of Magnetic . . . etc.," IEEE Trans. on Magnetics, Sep. 2003, pp. 3232-3234, vol. 39(5).

Shaheen, N., et al., "Gastroesophageal Reflux, Barrett Esophagus, and Esophageal . . . etc.," J. Am. Med. Assoc., Apr. 2002, pp. 1972-1981, vol. 287.

Simon, M.D., et al., "Diamagnetically Stablized Magnet Levitation," Amer. Journ. of Phys., Jun. 2001, pp. 702-713, vol. 69(6).

Smout, A.J., "Manometry of the Gastrointestinal Tract: Toy or Tool?" Scandinavian Journal of Gastroenterology Suppl, Nov. 2001, pp. 22-28, vol. 36.

Spiess, A.E., et al., "Treating Achalasia: From Whalebone to Laparoscope," J. Am. Med. Assoc., Aug. 1998, pp. 638-642, vol. 280.

Srinivasan, R., et al., "Esophageal Function Testing Using Multichannel . . . etc.," Amer. Journ. Physiol.: Gastro. and Liver Phys., Mar. 2001, pp. G457-G462, vol. 280.

Fischer, D., et al., "Capsule Endoscopy: The Localization System," [abst], Gastrointestinal Endoscopy Clinics of North America, Jan. 2004, pp. 25-31, vol. 14.

Gavriel, J., et al., "History and Development of Capsule . . . etc.," Gastrointestinal Endoscopy Clinics of North America, Jan. 2004, pp. 1-9, vol. 14.

Geim, A.K., et al., "Diamagnetic Levitation . . . etc.," Journal of Applied Physics, May 2000, pp. 6200-6204, vol. 87(9).

Geim, A.K., et al., "Magnetic Levitation at Your Fingertips," Nature, Jul. 22, 1999, pp. 323-324, vol. 400.

Geim, A.K., et al., "Of Flying Frogs and Levitrons," European Journal of Physics, Jul. 1997, pp. 307-313, vol. 18(4).

Gerson, L.B., et al., "Patient-Derived Health State Utilities . . . etc.," American Journal of Gastroenterology, Mar. 2005, pp. 524-33, vol. 100.

Glukhovsky, A., "Wireless Capsule Endoscopy," Sensor Review, 2003, pp. 128-133, vol. 23(2).

Gonzalez, J.L., et al., "Friction-Assisted Magnetic Holding . . . etc.," Proc. of the 28th IEEE EMBS Annual Int'l Conf., Aug. 30-Sep. 3, 2006, pp. 5944-5947, New York, USA.

Gonzalez, J.L., et al., "Integrated Esophageal Pressure, pH and Bolus Transit Sensor," Proc. IEEE Sensors, Oct. 2004, pp. 1369-1372, vol. 3, Vienna, Austria.

Goyal, R.K., et al., "Pressure Inversion Point at the Upper High Pressure Zone and its Genesis," Gastroenterology, Apr. 1970, pp. 754-759, vol. 59.

"Hall Effect Sensing and Application", Honeywell, Inc., <http://content.honeywell.com/sensing/prodinfo/solidstate/technical/hallbook.pdf>, [retrieved Jan. 11, 2007].

Holloway, R.H., et al., "Electrical Control Activity of the Lower Esophageal . . . etc.," Am. J. Physiol. Gastroint. Liver Physiol., Apr. 1987, pp. G511-G521, vol. 252.

Hu, C., et al., "Efficient Linear Algorithm . . . etc.," IEEE EMBS 27th Annual International Conference, Sep. 2005, pp. 7143-7146, Shanghai, China.

Hu, C., et al., "Efficient Magnetic Localization . . . etc.," IEEE/RSJ Int'l Intelligent Robots and Systems Conference, Aug. 2005, pp. 628-633, Edmonton, Canada.

Hu, C., PhD Thesis, University of Alberta, Spring 2006, Edmonton, Alberta.

Johnson, L.F., et al., "Development of the 24-Hour Intraesophageal pH Monitoring Composite Scoring System," Journal of Clin. Gastroenterology, 1986, pp. 52-58, vol. 8, USA.

Jui, Y.T., et al., "The ESO-Pill: A Non-Invasive MEMS Capsule . . . etc.," Proc. 2004 11th IEEE Int'l Conf. Elect. Circ. and Syst., Dec. 2004, pp. 427-430, Tel Aviv, Israel.

Kahrilas, P., et al., "American Gastroenterological Association Technical Review on the Clinical . . . etc.," Gastroenterology, Dec. 1994, 1865-1884, vol. 107, Chicago.

Kahrilas, P., et al., "Clinical Esophageal pH Recording: A Technical Review for Practice . . . etc.," Gastroenterology, Jun. 1996, pp. 1981-1996, vol. 110, Illinois, USA.

Stein, H.J., et al., "'Efficacy' of Esophageal Peristalsis: A Manometric Parameter . . . etc.," Diseases of the Esophagus, Dec. 2004, pp. 297-303, vol. 17.

Stendal, C., "Practical Guide to Gastrointestinal Function Testing," Stockholm: Blackwell Science Ltd., 1997.

Thompson, H., et al., "Eddy Current Magnetic Levitation . . . etc.," IEEE Potentials, Feb. 2000, pp. 42-44, vol. 19(1).

Tibbling, L., et al., "Dysphagia and its Consequences in the Elderly," Dysphagia, Dec. 1991, pp. 200-202, vol. 6(4).

Tutuian, R., et al., "Multichannel Intraluminal Impedance in Esophageal Function . . . ," Journal of Clinical Gastroenterology, Sep. 2003, pp. 206-215, vol. 3, Charleston, USA.

Wang, W., "A Study on RF Based . . . etc.," IEEE Mechatronics and Automation 2006 International Conference, Jun. 2006, pp. 1663-1667, Luoyang, China.

Wang, X., "Physiological Factors of the Small . . . etc.," IEEE EMBS 27th Annual International Conference, Sep. 2005, pp. 2942-2945, Shanghai, China.

Weusten, B.L.A.M., et al., "Spatiotemporal Characteristics of Physiological Gastroesophageal Reflux," Mar. 1994, American Journal of Physiology, pp. G357-G362, vol. 266, USA.

Wikipedia, the Free Encyclopedia, "Magnetic Levitation," Jun. 21, 2005, <http://en.wikipedia.org/wiki/magnetic_levitation> [retrieved Jan. 11, 2007].

Wu, B., U.S. Appl. No. 60/719,887, filed Sep. 23, 2005.

Xie, X., "Micro-System Design . . . etc.," IEEE EMBS 27th Annual International Conference, Sep. 2005, pp. 7135-7138, Shanghai, China.

Yi, J.H., et al., "Robust Force Control for a Magnetically Levitated . . . etc.," Journal for Control Engineering Practice, 1996, pp. 957-965, vol. 4(7).

Zvi, F., et al., "Future of Capsule Endoscopy," Gastrointestinal Endoscopy Clinics of North America, Jan. 2004, pp. 219-227, vol. 14.

Abell, T.L., et al., "Glucagon-Evoked Gastric Dysrhythmias I . . . etc.," [abst] Gastroenterology, Jun. 1985, pp. 1932-1940, vol. 88.

Al-Zaben, A., et al., "Analysis of Intraluminal Impedance Measurements," Physiological Measurements, Nov. 2003, pp. 837-845, vol. 24.

Al-Zaben, A., et al., "Computation of Intraluminal Impedance," Physiological Measurements, Feb. 2004, pp. 61-70, vol. 25, England.

Asher, G.M., et al., "An Equivalent Circuit Approach . . . etc.," IEEE Transaction on Magnetics, Mar. 1982, pp. 692-697, vol. 18(2).

Barie, W., et al., "Linear and Nonlinear State-Space . . . etc.," Int'l Journal of Systems Science, Nov. 1996, pp. 1153-1163, vol. 27(11).

Baschirotto, A., et al., "A Fluxgate Magnetic Sensor . . . etc.," IEEE Transactions on Instrumentation and Measurement, Feb. 2007, pp. 25-31, vol. 56(1).

Bredenoord, A.J., et al., "Minimum Sample Frequency for Multichannel Intraluminal . . . ," Neurogastroenterology and Motility, Dec. 2004, pp. 713-719, vol. 16, The Netherlands.

Bredenoord, A.J., et al., "Reproducibility of Multichannel Intraluminal Electrical . . . etc.," American Journal of Gastroenterology, Feb. 2005, pp. 265-269, vol. 100.

Brin, M.F., and D. Younger, "Neurologic Disorders and Aspiration," Otolaryngol Clin North Am, Nov. 1988, pp. 691-699, vol. 21.

Brondsted, H., et al., "Cross-Linked Dextran—A New Capsule Material for Colon Targeting of Drugs," Journal of Controlled Release, Apr. 30, 1998, pp. 7-13, vol. 53.

Cave, D.R., "Reading Wireless Video Capsule Endoscopy," Gastrointest Endosc Clin N Am, Jan. 2004, pp. 17-24, vol. 14.

Chiba, A., et al., "Magnetic Actuator for Capsule . . . etc.," IEEE Int'l Magnetic Conference, Apr. 2005, pp. 1251-1252, Nagoya, Japan (abstract).

Cibula, E., et al., "Miniature Fiber-Optic Pressure Sensor With a Polymer Diaphragm," Applied Optics, May 2005, pp. 2736-2744, vol. 44.

De Franchis, R., "Small Bowel Malignancy," [abst] Gastrointestinal Endoscopy Clinics of North America, Jan. 2004, pp. 139-148, vol. 14.

Donlagic, D., et al., "All-Fiber High-Sensitivity Pressure Sensor With $SiO_2$ Diaphragm," Applied Optics, Aug. 2005, pp. 2071-2073, vol. 30.

Fajardo, N.R., et al. "Esophageal Perforation After Placement of Wireless Bravo pH Probe," Gastrointest Endosc, Jan. 2006, pp. 184-185, vol. 63(1).

Fass, J., et al., "Measuring Esophageal Motility with a New . . . etc." (abstract), Scand. Journal of Gastroenterology, Aug. 1994, pp. 693-702, vol. 29, Norway.

Fass, R., et al., "Effect of ambulatory 24-hour esophageal pH monitoring on reflux-provoking . . . etc.", Digestive Diseases and Sciences, Nov. 1999, pp. 2263-2269, vol. 44.

* cited by examiner

MAGNETIC LEVITATION OF INTRALUMINAL MICROELECTRONIC CAPSULE

CROSS-REFERENCE TO RELATED APPLICATIONS

This application claims the benefit under 35 USC 119(e) of U.S. provisional patent applications 60/643,392 filed Jan. 11, 2005 and 60/719,887 filed Sep. 23, 2005, the content of each of which is hereby incorporated by reference.

FIELD OF INVENTION

The present invention is related to apparatus and methods for intraluminal inspection of internal organs of a human or animal body, and more specifically to affixing or positioning and further controlling or steering autonomous microelectronic capsules equipped with one or more sensors for monitoring postion of the capsule in lumens of internal organs and with one or more sensors for sensing one or more physiological condition(s) in the internal organs and with means for communicating such position and physiological information or data to receiver means outside the body.

BACKGROUND OF INVENTION

The possibility for using smart pills or miniature microelectronic capsules which have the capability to transmit diagnostic data from the gastrointestinal (GI) tract has been the subject of increasing scholarly and practical interest. Alternatively to the capsule endoscopy concept, new smart pill designs do not necessarily have to include imaging modality, since many other physiological, electrical, chemical, and mechanical phenomena in internal organs in general, or in the gut in particular (for example, pH, pressure, intraluminal impedance, etc.) could be investigated using this-non-invasive technique.

Examples of magnetically driven capsules used in human body diagnosis and treatment include: Ueda, U.S. Pat. No. 5,681,260, which describes a capsule type endoscope that carries a video camera, transmitter, receiver and magnet. The transmitter and receiver communicate with an exterior transmitter and receiver to deliver video images to a display. An exterior magnetic force generator with a capsule locating sensor and controller controls magnetic force on the magnet and hence on the capsule. Temperature and pH sensors may be carried on the capsule. Jin, U.S. Pat. No. 6,776,165, describes a navigation system and navigatable capsules which are useful for remote-controlled imaging, biopsy and programmable drug release within the body of an animal. The components of the system comprise a capsule dimensioned and shaped to move within the body. An anisotropic magnetic component is mechanically coupled to the capsule to move or orient the body in relation to an applied magnetic field, and a magnetic field generating system external of the body generates a three dimensionally oriented magnetic field within the body to move or orient capsule. Wakefield, 2004, US Pat App. 20040199054, discloses a general concept of magnetically propelled capsule endoscopy, including the concept of using magnets for movement and directional control and position sensors. It envisions control by an externally-generated magnetic field.

However, the issue of controlled affixing (holding) or steering such microelectronic capsules to and from particular positions in the gastrointestinal (GI) tract has not been satisfactorily resolved by these teachings.

SUMMARY OF THE INVENTION

Diamagnetically-stabilized magnetic levitation is utilized as part of this invention to affix and/or steer autonomous devices, such as swallowed microelectronic capsules, in the lumens of internal organs. A set of external solenoids circumferentially arranged around a human body that contains the swallowed capsule can significantly ease the requirements for levitating and further controlling the said capsule by (1) moving the said solenoids, (2) moving the patient with respect to said solenoids, or (3) manipulating the electrical current through said solenoids in a controlled fashion, in order to steer and move the capsule in the internal organs of interest.

The capsule can provide the necessary feedback for its own location control by continuously reporting one or more of the following parameters: the pressure exerted upon it, its acceleration (which practically would reflect the extent of the impact of gravitational forces on the capsule), its velocity, and its position. Any or all of these feedback parameters of pressure, acceleration, velocity, and position can be used for assessing and controlling the location of the capsule and for assessing the gravitational and motility forces exerted upon it, so that necessary steering, movement, and stability control of the capsule by the external magnetic field can be accomplished. The capsule is affixed, i.e., held in position, by diamagnetic levitation, and steering is accomplished by changing the external magnetic field exerted on the levitating capsule. When a location of the capsule is determined to be not where it is desired to be, the magnetic field of the solenoid in relation to the capsule can be varied in a manner that steers and moves the capsule to such desired location and then affixed or held in that desired location.

The capsule references cited above do not disclose any concept of the capsule itself being levitated nor do they disclose any concept of or means for affixing or positioning the capsule at a particular location or any precise control of position and steering of the capsule. For example, in a large-lumen organ, with the simple magnetic control envisioned in Wakefield for example, and in the absence of levitation, the capsule would lean to one side of the wall of the lumen, and steering it within the lumen would be impossible. Full capsule control, including affixing the capsule at a particular location and holding it there for a controlled period of time, is theoretically possible with simple magnetic levitation. Some simple magnetic levitation techniques, however, require low temperatures and superconductors, which would not be practical for applications in intraluminal capsule endoscopy. In contrast, the method for diamagnetic levitation disclosed here overcomes this problem, achieving intraluminal positioning of a capsule in the body using a small permanent magnet located inside the capsule with a diamagnetic shell.

There is also provided in accordance with an aspect of the invention a diamagnetially levitatable intraluminal microelectronic capsule, comprising a housing of a size and shape suitable for swallowing by a human being, a magnet carried by or forming part of the housing, diamagnetic material carried by or forming part of the housing; and a therapeutic or diagnostic element carried by or forming part of the housing.

A small permanent magnet used in this invention may be mounted within a capsule or can be part of the capsule, the shell of which is made of appropriate diamagnetic material, or contains a layer of such material with an appropriate thickness. Alternatively, the wall of the organ in which the monitoring is to occur can serve as a diamagnetic material facilitating the levitation. The capsule of the present invention is controlled by an external magnetic field produced by solenoids. The topology of this field is manipulated by changing the current through the solenoids or by changing the relative position between the solenoids and the patient, rather than by moving permanent magnets with respect to each other using a screw.

BRIEF DESCRIPTION OF THE DRAWINGS

There will now be described preferred embodiments of the invention, with reference to the Figures, by way of example, in which.

DETAILED DESCRIPTION OF THE INVENTION

The word "solenoid" is used here according to its general meaning of a long coil through which electric current flows, thereby establishing a magnetic field with a North and South poles on each end of the said solenoid. Levitation is the process by which an object is suspended against any force acting upon it (in the case considered here, namely gravity or peristalsis), in a stable position by a force without physical contact. Changing the position of the applied force causing the levitation can bring about the controlled movement of the levitating body.

Figure 1:
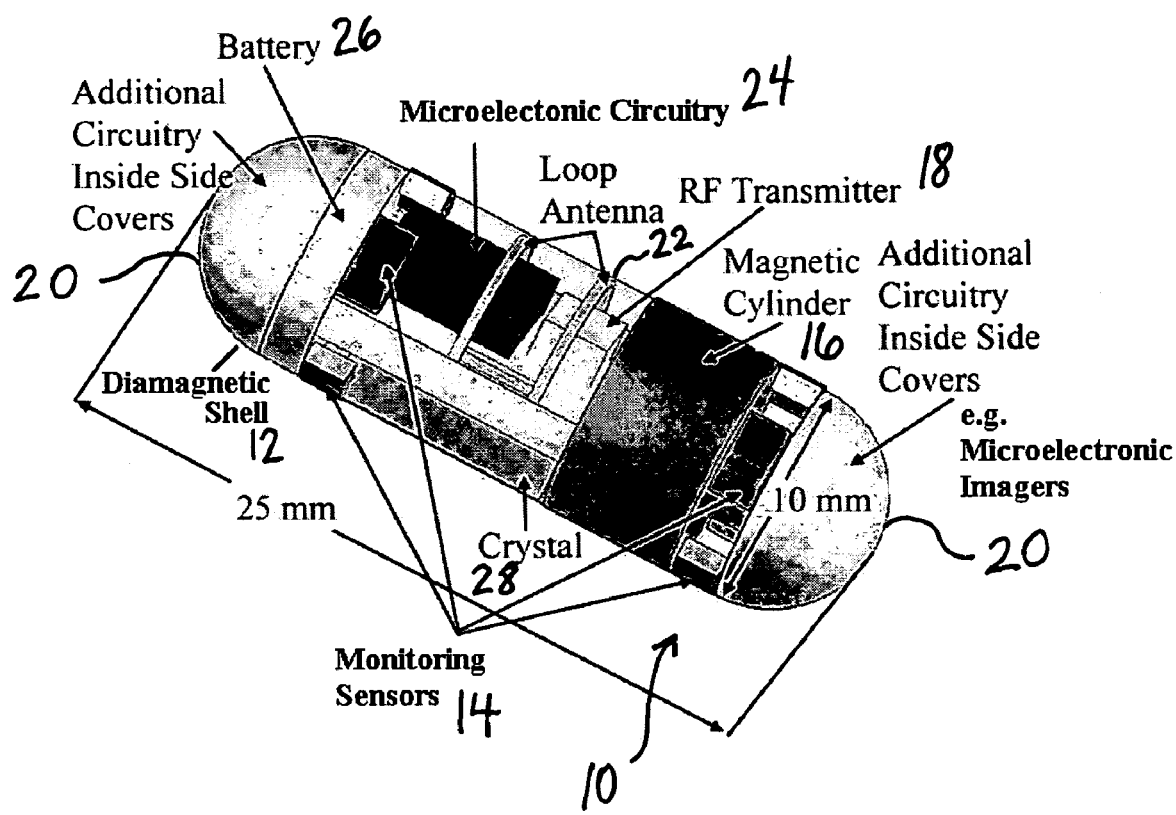
FIG. 1 presents the overall structure of one possible embodiment of an intraluminal device taking advantage of the method of this invention.

Referring to FIG. 1 a diamagnetically levitatable intraluminal microelectronic capsule 10 is shown that is comprised of a shell 12 of the capsule, which may or may not contain a cylinder of appropriate diamagnetic material (e.g. bismuth, antimony, pyrolytic graphite, carbon graphite, gold, etc.), microelectronic components or sensors 14 related to the testing or monitoring function of the capsule in the body, for example pH monitoring electrode, CMOS imaging sensors, impedance-monitoring sensors, accelerometers, pressure sensors, etc; a miniature magnet 16 (for example, made of NdFeB, an alloy of neodymium, iron and boron), which is contained in or a part of the capsule 10; and a radio-frequency (RF) transmitter 18. The capsule 10 has a shape and size suitable for swallowing, for example by the provision of rounded ends 20, which may contain additional microelectronic devices such as imagers. The sensors 14 may be used for sensing acceleration, impedance, pH, pressure, imaging, or other parameters that are useful in characterizing and/or diagnosing maladies of gastrointestinal tracts. The radio-frequency (RF) transmitter 18 for transmits data sensed by components in the capsule relating to the functions and features monitored to a receiver located outside the test subject's body, and is provided with a suitable antenna 22 such as a loop antenna. Microelectronic circuitry 24 and crystal 28 for the transmitter and sensors may also be carried on or within the capsule 10 and may be formed as part of the shell or housing 12 of the capsule 10. A battery 26 or other suitable power source, such as an inductor for transducing electric or magnetic fields to electric power, may also be carried on or within the capsule 10.

In order to provide meaningful and sufficiently long testing or monitoring function within the lumen of some internal organs (for example, but not limited to, impedance, pH, or pressure monitoring in the esophagus, the stomach, the small intestine, the colon, and/or the rectum), the capsule is either affixed at a particular location, or/and it has to be steered to a particular location or to multiple locations in a controlled fashion. Prior art invasive ways to control the motion and the position of the capsule are generally less desirable than the non-invasive control and steering provided by this invention. Relying only on the naturally existing propulsive peristalsis of the GI tract is at least sometimes insufficient to cause the capsule to be at a certain diagnostically and clinically important position for a long and controlled period of time.

To solve this problem, the capsule of this invention can be affixed at a given location using diamagnetically stabilized magnetic/electromagnetic levitation using solenoids 32, 34 (FIG. 3) or a strong DC magnet. Because of the relatively low power consumption of the capsule, it can be power supplied either directly with a battery 26 in the capsule or transcutaneously using electromagnetic inductance. The transmitting coil 32, 34 can be located anywhere outside the patient's body 36 in close enough proximity to the said body, including, but not limited to, a belt or a vest 38 worn by the patient. The belt 38 may also hold one or more batteries 40 for the solenoids 32, 34, as well as one or more controllers 42 for controlling the current provided to the solenoids 32, 34. An external solenoid 32, 34, which is also necessary for the steering and motion control, must also be positioned adjacent the patient's body in close enough proximity to the body 36 so that the magnetic field is effective for the capsule levitation and steering operation. Therefore, the external solenoid 32, 34 can also be mounted with the belt or vest 38. The receiving coil for the capsule power supply is preferably wrapped around the inner circumference of the capsule 10 or pill in a spiral fashion. A data logger 44 with a receiver for communicating with the transmitter 18 may be carried by the person 36 for receiving position and sensor data from the capsule 10. The data logger 44 may be used to send data to the controllers 42, or the controllers 42 may receive and process signals directly from sensors in the capsule 10. Communication between any of the electric circuit elements described in this patent document, which are typically represented by lines on the drawings, may be wired or wireless and may use conventional communication links. Specifically, the controllers disclosed here, such as the control circuits 42, 56, 58 and 78 may use conventional wired or wireless communication links to receive sensor inputs, such as from positional sensors, and to deliver control signals to the solenoids 32, 34, 52, 54 and/or actuators 62, 64. The specific embodiments disclosed here are intended to be exemplary. The controllers 42, 56, 58 and 78 may have suitable conventional RF receivers or interfaces associated with them or contained within them to allow communication with the sensors, such as position or physiological sensors, in the capsule 10.

Motion control using diamagnetic levitation is used for positioning and steering the capsule in this invention. M. Simon and his coworkers have reported, for example in A. K. Geim, M. D. Simon, M. I. Boamfa, L. O. Heflinger, "Magnet Levitation at your Fingertips," *Nature*, vol. 400, pp. 323-324, 1999 and M. D. Simon, L. O. Heflinger, A. K. Geim, "Diamagnetically stabilized magnetic levitation," *American Journal of Physics*, vol. 69(6), pp. 702-13, 2001 (hereafter "Simon"), an important advance in magnetic levitation with the application of the stabilizing effect of diamagnets surrounding a miniature magnetic cylinder. Essentially, the intrinsically unstable equilibrium when applying an external magnetic force to lift a magnetic object, such as the magnet in the capsule, can be stabilized by the repulsive forces created by diamagnetic materials (known as diamagnets) surrounding the magnetic object to effectively levitate the object. This principle is used in this invention to position and steer a diagnostic capsule 10 in an internal organ, such as in the gastrointestinal tract.

The wall 30 of an internal organ (e.g., the esophagus, see FIG. 2) may serve the diamagnetic function in this invention. In the example of the esophagus, in order to achieve stable levitation, the applied magnetic force MB'(z) has to compensate the sum of the peristaltic force $f_p$ in the esophagus, and the gravitational force mg (where m is the mass of the entire pill, not only of the miniature cylindrical magnet, and g is the gravitational force). M is the vector of the magnetic moment, M(z) is its component along the z-axis, B is the vector of the magnetic field in space, B(z) is its component along the z-axis, and B'(z) is its first derivative. Worst case scenario is assumed with the patient standing (i.e. the gravitational force is maximal). The total energy U of the magnet then is:

$$U = -M \times B + (mg + f_p)z + U_{dia} \tag{1}$$

where $U_{dia}$ is the energy of diamagnetic interaction with the miniature magnet. For a stable equilibrium, this energy should be at a minimum ($\Delta U > 0$). The peristaltic force can be easily calculated in real time considering the readings from the pressure sensor and the surface area over which this pressure has been measured or applied. Equation (1) can be elaborated further [see Simon] to show that a miniature magnetic object several millimeters in size can be levitated with a clearance gap of several millimeters using an external magnetic field created by a 10-cm solenoid and a ring of strongly diamagnetic material, such as bismuth, surrounding the miniature magnetic object. In Simon, however, only the gravitational force, but not naturally occurring peristaltic force was considered. When discussing the physical phenomena in the gut, the peristaltic force as measured by a pressure sensor mounted on a pill or capsule has to be added as well as gravitational force if the patient is standing. Should the patient lie down, the gravitational force has to be either taken out from the equation, or it should be substantially and adequately reduced. The gravitational force can be easily monitored by an accelerometer, which is also mounted in the pill or capsule as well. Monitoring sensors 14 (see FIG. 1) can include position, pressure, impedance, pH, imaging, and accelerometer sensors. An RF transmitter 18 and loop antenna 22 are also provided in the capsule to transmit signals or data from the capsule in the esophagus to a RF receiver associated with a data logger 44 (FIG. 3) outside the patient's body. The data from the microelectronic sensors located in the capsule (for example, pH, impedance, CMOS imaging, pressure, acceleration or any other sensors or a combination thereof) are thus transmitted to the data logger 44.

Thus, a real-time feedback of both the peristaltic force and the gravitational force influencing the pill or capsule 10 inside the esophagus 30 can be transmitted to a receiver for logging and/or processing outside the patient's body. Using this feedback, the topology of the external magnetic field can be manipulated by any one or a combination of three different mechanisms: (1) moving the external solenoids with respect to the body of the patient; (2) moving the position of the patient with respect to the external solenoids; and (3) by changing the electrical currents in the respective solenoids, thus changing the topology of the magnetic fields created by them so that the capsule stays in place, or, alternatively, is displaced in a controlled fashion to a new location in which levitational stability is achieved (FIG. 4).

Figure 4:
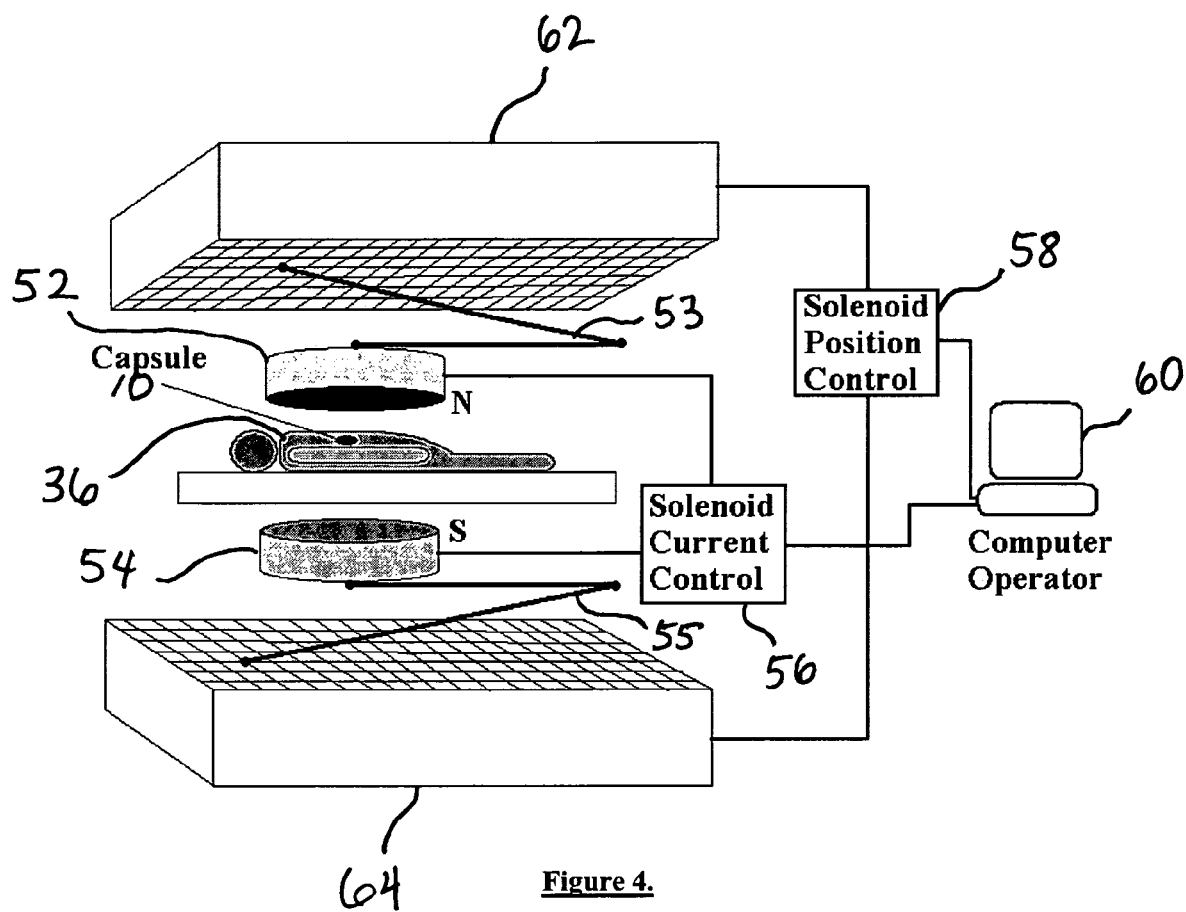
FIG. 4 depicts an embodiment of the concept of steering the swallowed microelectronic capsule using two external solenoids.

FIG. 4 shows an example in which solenoids 52, 54, similar to solenoids 32, 34, are supported by articulating arms 53, 55 about a patient 36 who has swallowed a capsule 10. Current is supplied to the solenoids 52, 54 to levitate the capsule 10 via solenoid current controllers 56, 58, which are controlled by a computer operator 60. The computer operator 60 also supplies signals to actuators 62, 64 for the articulating arms 53, 55.

The computer operator 60 controls the positions of the solenoids 52, 54 with respect to the levitating capsule 10 and/or the respective electric currents through the solenoids 52, 54. With a gradual control of the positions of the solenoids 52, 54 and/or of the currents through them, the topology of the magnetic field levitating the capsule 10 changes, so that the capsule levitation position changes. This change in the topology of the external magnetic field can be achieved by (1) dynamic re-positioning of the external solenoids; (2) dynamic re-positioning of the patient with respect to the said external solenoids; or (3) dynamic change in the currents flowing through the solenoids. Persons having ordinary skill in the art know how to control movements of magnets with respect to persons or vice versa and how to control electric current flow through solenoids, as well as how to use actual positions from the capsule as feedback to actuate such controls to steer or position the capsule, once they understand the principles of this invention.

Since the peristaltic force is dynamically added to the gravitational force, the required magnetic force to overcome the peristaltic and gravitational forces to levitate the capsule is higher than the one reported by Simon. Therefore, the external solenoid is preferably 2-3 times larger or more powerful than that reported by Simon. In the worst case scenario, a maximal propulsive peristaltic pressure of 300 mmHg with the patient standing should be anticipated. Considering a surface area over which this peristaltic pressure is applied to be $4\pi(0.005^2)/2 = 0.000157 \, m^2$ for a capsule size, for example, as shown in FIG. 1, and the conversion of 1 mmHg=133.224 Pa, the peak value of the peristaltic force on the capsule shown in FIG. 1 can be overestimated at 6.27 N. The maximal gravitational force for a capsule or pill with weight of 25 g is about 0.25N. Therefore, a maximal force $f_m = 7$ N is an overestimation of the required counterforce to achieve levitation of the capsule shown in FIG. 1. This force can be exerted on the built-in miniature magnet that is within or part of the capsule or pill, such as the magnetic cylinder shown in FIG. 1, so that the entire capsule is levitated, and can be moved by changing the topology of the external magnetic field, which changes the location of the levitational equilibrium thus causing the movement of the levitating permanent magnet to this new location.

Following the derivations proposed by Simon, the total energy of the magnet at equilibrium can be given with:

$$U \approx U_0 + [mg + f_m - MB'(z)]z + K_v z^2 + K_h r^2 + Cr^2 \quad (2)$$

where $K_v(z) \equiv -MB''(z)/2$, $K_h(z) \equiv -M[B'(z)^2 - 2B(z)B''(z)]/8B(z)$, and $r^2 = x^2 + y^2$ in a three-dimensional Cartesian system of coordinates. The presence of a diamagnetic material surrounding the capsule (part of the tubular esophageal wall according to one embodiment of this invention) is reflected by the last term in Eq. 2. For this configuration it was previously determined [Simon] that $$C = 45\mu_0|\chi|M^2/16D^5 \quad (3)$$

where $\mu_0$ is the magnetic permeability in the medium, which in the present derivation for simplicity will be considered free space, $\chi$ is the magnetic susceptibility of the surrounding medium (approximately $-10^{-5}$ for body tissue), and D is the diameter of the esophageal tube (approximately 2.5 cm). The minimum of the energy U, and therefore, stable levitation, can be achieved if:

$$C > MB'(z)^2/8B(z) \quad (4)$$

just above the point of maximum field gradient $B''(z)=0$, which represents the optimal levitation point. Depending on the external solenoid used (long or short, circumferential or planar), a characteristic scale L on which the field changes ($B'=B/L$) can be introduced which varies between R and 1.2R for long and short solenoid respectively, R being the radius of the solenoid. The levitating magnet (e.g., the magnetic cylinder in FIG. 1) can be approximated as a sphere of diameter d and a remnant field Br (about 1 Tesla for a 4-mm diameter magnet) because of its small size and to ease the computational complexity. Then $$M = (\pi/4\mu_0)B_r d^3 \quad (5)$$

and the requirement for levitation modified from the one given by Simon becomes:

$$A(|\chi|LB_r^2 d^3/\mu_0 \rho 25\ g)^{1/5} > D > d \quad (6)$$

where $\rho$ is the density of the magnetic material, A is a scaling factor of 1.02, and the factor 25 in the denominator accounts for the peristaltic force, since the gravity force was calculated to be about 25 times smaller than the peristaltic force. Keeping the difference D–d the same as in Simon, a magnet with dimensions twice as big compared to the one used by Simon in their first experiment, i.e. d=8 mm, provides an 8 times increase in the numerator of Eq. 6. Considering the fact that in our case the scaling factor A is twice as small compared to the one utilized in Simon and the 15-times reduced magnetic susceptibility in the absence of a bismuth cylinder, the solenoid needed to provide levitation of the capsule in FIGS. 1 and 2 in the esophagus increases in dimensions about 100 times as compared to the 10-cm solenoid used in Simon. In contrast, in the presence of a diamagnetic shell deposited on the inner wall of the capsule encompassing the miniature magnet, this increment would be 3.12 times, thereby allowing the use of two solenoids with a radius R=31-32 cm, which is quite feasible for mounting in a vest worn by the patient as illustrated in FIG. 3 (for affixing the capsule at a particular location).

Alternatively, the capsule or pill itself can be produced of a stronger diamagnet than bismuth such as pyrolytic graphite. For steering the levitating capsule, a more elaborate external setup is needed, involving rotating and/or linearly moving the solenoids in the vicinity of the patient and encompassing the capsule as shown in FIG. 4. The levitating position of the small permanent magnet located in the microelectronic capsule 10 shelled by strong diamagnetic material such as bismuth or pyrolytic graphite can change in a controlled fashion if the topology of the external magnetic field changes. Such change in the field topology can be induced by any one or a combination of (1) changing the relative position between the patient's body and the external solenoids by displacing the said solenoids in controlled fashion; (2) changing the relative position between the patient's body and the external solenoids by displacing the patient's body in controlled fashion; and (3) changing the currents in the solenoids thus manipulating the magnetic field created by each solenoid (see FIG. 4).

Figure 2:
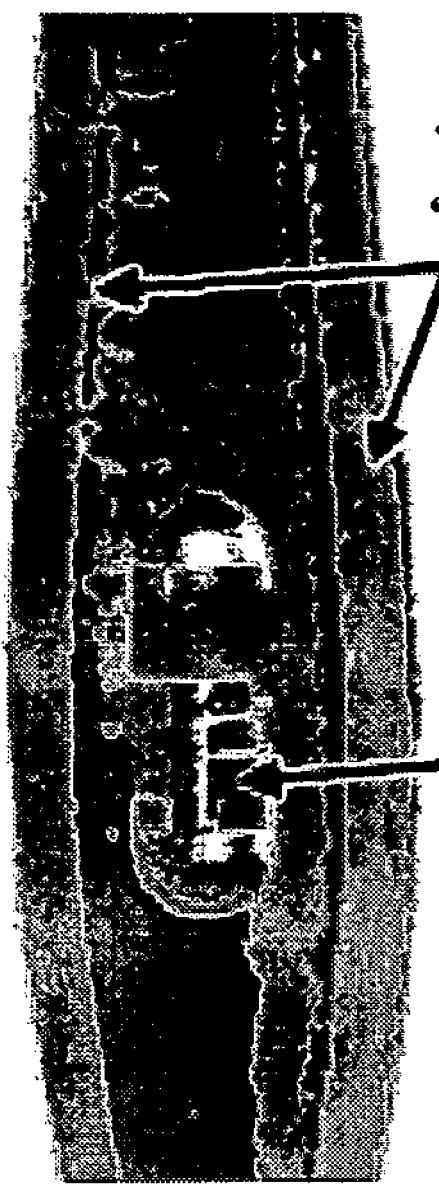
FIG. 2 illustrates the affixing, i.e., holding in position, of the capsule inside the lumen of an internal organ, for example the esophagus.
Figure 3:
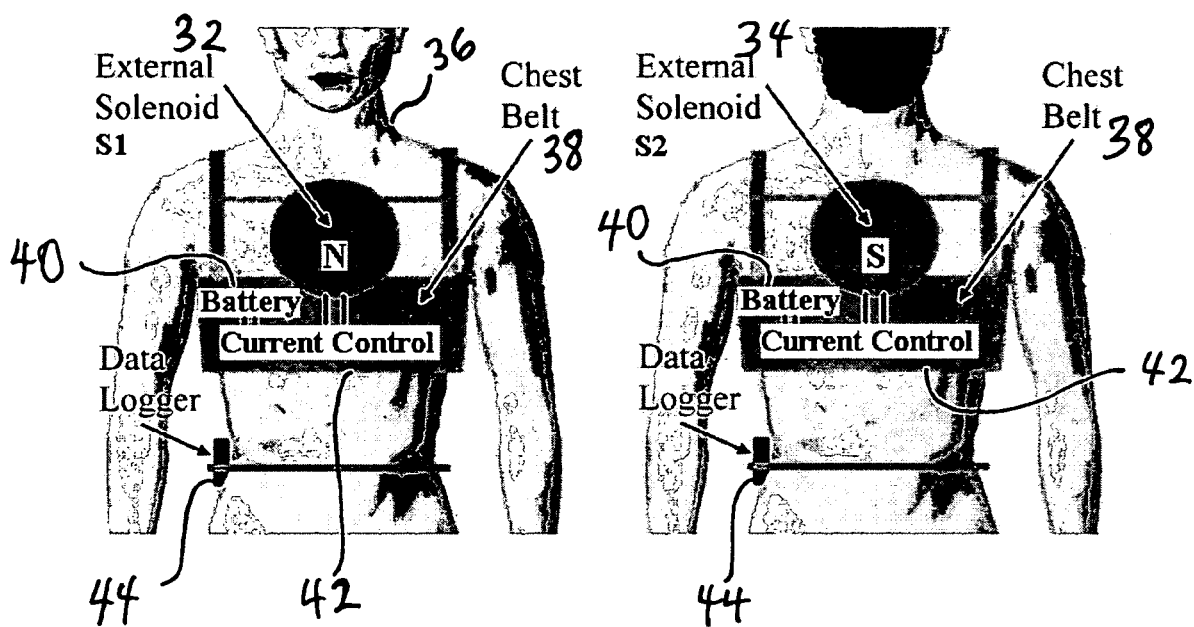
FIG. 3 gives an example of one embodiment of the invention with the capsule affixed, i.e., held in position, above the lower esophageal sphincter (LES) using horizontal diamagnetically-facilitated levitation with the help of two external solenoids (one at the front and one at the back of the patient's body) mounted in a vest worn by the patient throughout the test.
Figure 5:
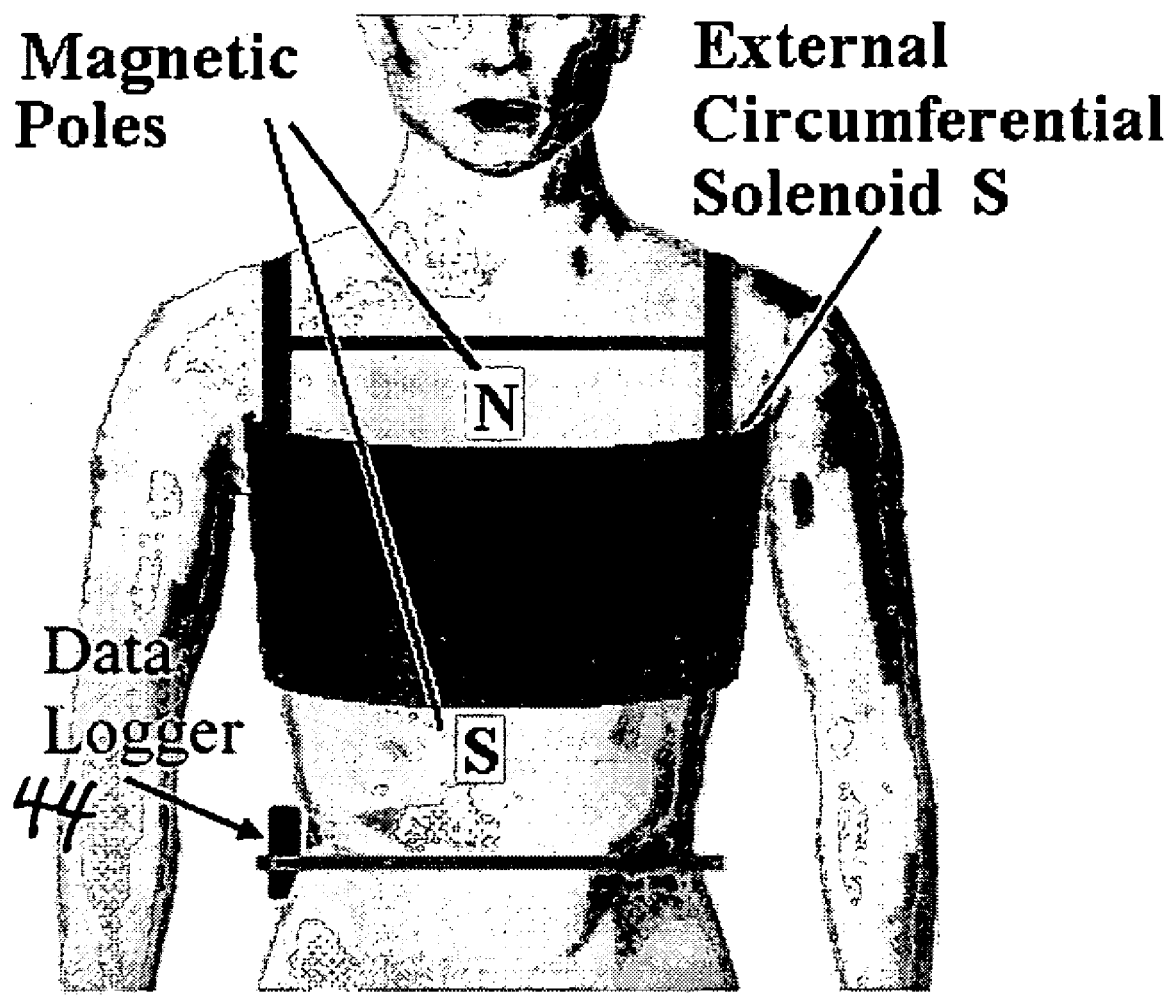
FIG. 5 depicts another embodiment of the invention with showing the capsule affixed above the lower esophageal sphincter (LES) using vertical diamagnetically-facilitated levitation of the swallowed capsule with the help of one circumferential solenoid mounted in a vest worn by the patient throughout the test.

Levitating the capsule in the esophagus, as illustrated in FIG. 2, in the absence of a bismuth or other diamagnetic layer in the shell of the capsule is another alternative, which is based on the fact that the walls of the organ of the body in which the capsule is levitating are also of diamagnetic material, although it is not as strong as the bismuth shell. Thus, stronger external solenoids are needed to achieve stable levitation. This can be achieved if, in the vest surrounding the body, we position one fully circumferential solenoid S, as illustrated in FIG. 5, to achieve the same stabilizing effect. Thus, the circumferential solenoid S in FIG. 5 is sufficient to levitate the capsule in the esophagus, rather than having the need to include stronger diamagnetic material surrounding the miniature magnet in the capsule. The data from the microelectronic sensors located in the capsule 10 (for example, pH, impedance, CMOS imaging, pressure, acceleration or any other sensors or a combination thereof) are transmitted to an external data logger 44 via the wireless radio-frequency transmitter 18 in the capsule and a radio-frequency receiver associated with the data logger 44 outside the patient's body.

The position and navigation sensors or accelerometers, RF transmitter and receiver, battery, crystal, and other sensors used in the capsule 10 can be any suitable devices. The accelerometers may be one-axis accelerometers as well as two-axis or three-axis accelerometers, for force, velocity, and position determination. While there are many kinds of small or MEMS (micro-electro-mechanical systems) accelerometers and other small accelerometers that would work for this invention, such as piezo film, electromechanical servo, piezoelectric, liquid tilt, bulk micromachined piezoresistive, capacitive, micromachined capacitive, and others that are well-known and readily available, MEMS capacitive accelerometers may be used, such as the ADXL202E capacitive MEMS accelerometer available from Analog Devices, Inc., Norwood, Mass., which is believed to have some of the better attributes and characteristics for this application. Based on measuring principles, MEMS accelerometers can be segregated into two different types: piezoresistive and capacitive. In piezoresistive-based accelerometers, silicon resistors, which change electrical resistance in response to applied mechanical load, are connected in a Wheatstone bridge to produce a voltage proportional to the acceleration of the proof mass attached to the sensor housing. In contrast, in capacitive accelerometers acceleration is measured by the change in capacitance due to a moving plate attached to the proof mass. Capacitive accelerometers are more popular than piezoresistive designs due to several advantages they have, including high sensitivity, high resolution, low noise, low drift, stable DC characteristics, low power dissipation, and low temperature drift. For esophageal applications, a resolution of at least 6.88 cm/s$^2$ (10% of the minimal acceleration value in the esophagus) is essential, i.e. the accelerometer has to detect acceleration levels as low as 6.88 cm/s$^2$. This, along with the obvious power supply and dimension limits narrows the technological availability to our application. Hence, a miniature-sized capacitive MEMS accelerometer, featuring low power consumption and high resolution, is a suitable candidate for the pill 10, as for example the ADXL202E capacitive MEMS accelerometer from Analog Devices (Norwood, Mass.), which features also a low cost, an advantage that might become important if more than one pill has to be swallowed by the patient over a certain time period in order to provide averaged estimates of the bolus transit in the esophagus. Also, pressure, pH, and impedance sensors can be any suitable devices that are available commercially, for example, but not for limitation, from Sandhill Scientific, Inc., Highlands Ranch, Colo. USA, or that are described in other publications, for example, the impedance sensors described in U.S. Pat. No. 5,109,870 issued to Silny et al. The impedance sensors may be longitudinal or split ring sensors as described for example in U.S. patent application Ser. No. 11/163,342, filed Oct. 15, 2005, the content of which is hereby incorporated by reference. In a split ring sensor, the poles or electrodes of the sensor are separated and located around the circumference of a capsule.

To remotely monitor physiological parameters in real-time in the esophagus, a reliable and effective wireless radio frequency (RF) link has to be established. Since the size of the transmitter is important due to the limited space in the capsule, a monolithically integrated transmitter chip is favored. For example, the MAX1472 ASK transmitter from Maxim (Sunnyvale, Calif.) may be used. The MAX1472 is a crystal-referenced phase-locked-loop (PLL) transmitter which operates in the 300 MHz to 450 MHz frequency range (VHF/UHF). The transmitter is available in a 3 mm×3 mm SOT23 package and is capable of delivering +10 dBm output power with a current consumption of less than 9.1 mA. A small-loop antenna fabricated out of a copper trace on the PC board can be employed to emit the modulated signal, and with a careful design of the matching network, maximum performance of the transmitter may be achieved. In addition, the transmitter can be directly coupled to the output of the sensors, which reduces the cost and saves additional space by avoiding the conditioning circuitry. An ASK superheterodyne receiver such as MAX1470 or MAX1473 may be used to receive the transmitted data and send it to a data logger or one or more of the controllers.

When the position and trajectory of the capsule 10 (or the levitating magnet 16 inside) is measured and conveyed to a control system, the field of the electromagnets can be continuously adjusted via feedback control systems to keep the capsule in the desired position. A feedback control system to levitate a magnet is commercially available from G. Marsden, of Art-Tec, Maine, USA, and see "Levitation! Float objects in a servo controlled magnetic field," Nuts & Volts Magazine, pp. 58-61, September, 2003. A Hall Effect sensor tracks the position of the levitating magnet. The Hall Effect sensor produces an electrical signal based on the strength of the perpendicular component of the local magnetic field. As the distance between the sensor and the magnet increases, the signal produced by the sensor becomes weaker. The signal from the sensor controls the duty cycle of a pulse width modulated (PWM) signal, which in turn controls the current supplied to the electromagnet. The components of the kit are primarily a Honeywell Hall Effect Sensor, a PWM control, Motor Control IC and Solenoid. To calculate the forces when dealing with non-uniform magnetic fields and permanent magnets, a Computer-Aided-Design (CAD) system such as the Maxwell 3D (Ansoft, Pittsburgh, Pa.) may be used. Maxwell 3D is an interactive software package that uses finite element analysis to solve 3D magnetostatic problems. For the situation where the patient is in the supine position (FIG. 4), the levitation system responds to the movement of the magnet slightly below and slightly above the equilibrium position. When the magnet is above the equilibrium position, the control circuit decreases the coil current and, in effect, the magnetic field of the coil. The attractive magnetic force between the coil and the magnet decreases as a result, and the magnet is brought back to the equilibrium position by gravity. Similarly, when the magnet drops below the equilibrium position, the control circuit increases the coil current to lift the magnet back up. An exemplary Hall Effect sensor is the SS495A by Honeywell, which has a typical magnetic range of +/−670 gauss (10,000 gauss=1 T). The location of the Hall Effect sensor must be chosen carefully. For example, if the sensor is too close to the solenoid, the magnetic field at the location of the sensor would increase beyond the maximum limit of the sensor, leading to improper feedback and failed levitation. In the commercially available levitation kit, the Hall Effect sensor senses the location of the magnet. For the application to the human body proposed here, the magnetic field detected by the Hall Effect sensor comes from both the magnet 16 and the solenoids (32, 34, 52, 54). A Hall Effect sensor mounted outside the body may not detect the field of the magnet, no matter how sensitive the sensor is, because of the presence of the coil field, which is far greater in comparison. For human body applications, it may be preferable to sense the coil field strength with a Hall Effect sensor located in the capsule 10. Alternatively, a dual Hall Effect sensor system may be used.

Figure 6:
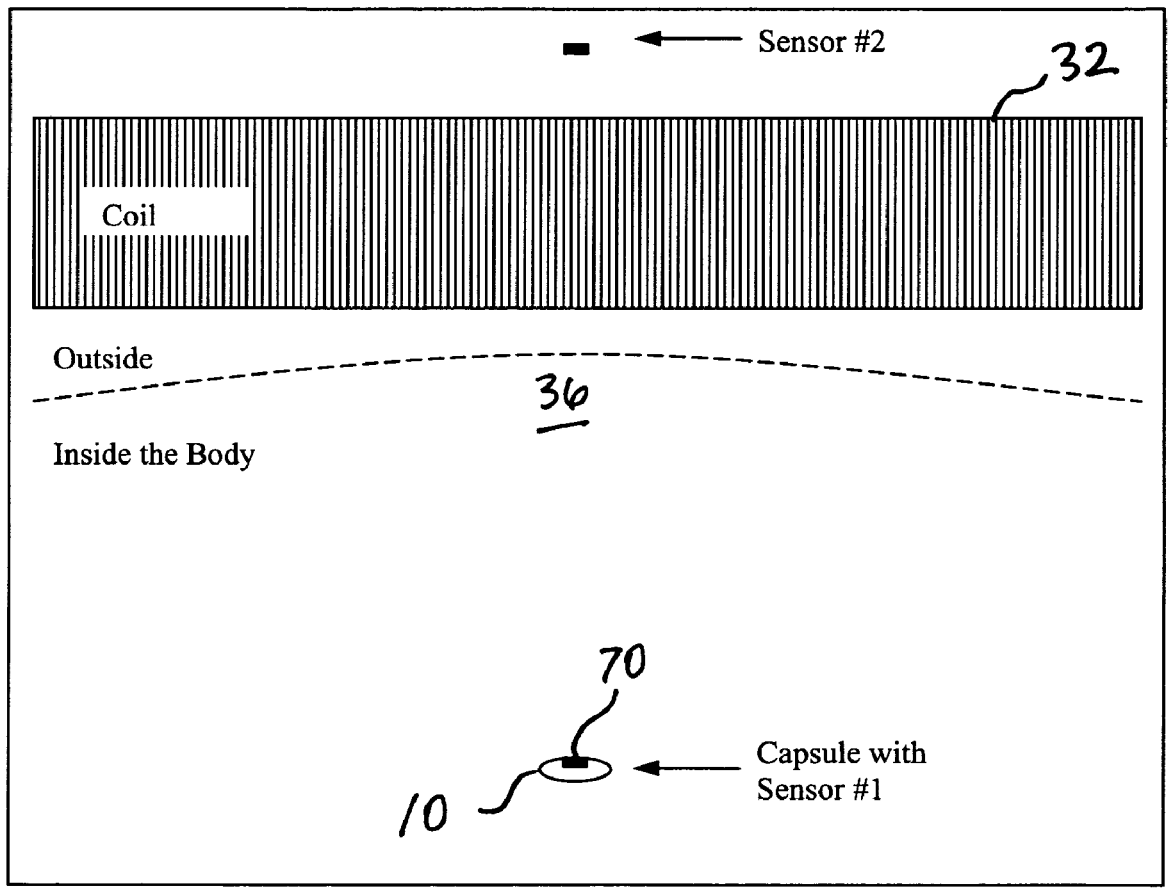
FIG. 6 shows a dual Hall Effect sensor of a feedback system for use in an embodiment of the invention.

In a dual sensor system as shown in FIG. 6, a first magnetic sensor 70 (one of elements 14 in FIG. 1 for example, or located in the rounded end covers 20) is embedded inside the capsule 10, while the second sensor 72 is positioned at a selected location outside the body. Sensor 72 produces voltage signal $V_2$, which represents $B_2$. The magnet 16 of capsule 10, being inside the body 36 and far away from sensor 72, has no influence on $V_2$. Sensor 70 produces voltage signal $V_1$ unadjusted, which represents the total magnetic field present inside the capsule 10 when it is at any position (equilibrium or deviated). The total magnetic field inside the capsule 10 is the sum of the fields produced by the magnet 16 and by the coil 32. Since the magnet 16 and sensor 70 are both inside the capsule 10, the magnetic field from the magnet remains the same with respect to sensor 70, regardless of the capsule position. Thus, a constant part of $V_1$ unadjusted is a result of the field of the magnet 16. This signal component is defined here as $V_m$. The resulting signal of adaptively removing $V_m$ from $V_1$ unadjusted is defined as $V_1$. $V_1$ does not represent $B_1$, unlike the case of $V_2$ representing $B_2$. This is because $V_1$ is for any capsule position, while $B_1$ is only for the capsule equilibrium position. $V_1|_{eq}$ can be used to denote the signal of sensor #1 in the specific case at the equilibrium position. Table 1 provides a list of defined variables and constants.

TABLE 1

Descriptions of the defined variables and constants

| Variable/Constant | Description |
| --- | --- |
| $B_1$ | Magnetic field produced by the coil at the capsule equilibrium position |
| $B_2$ | Magnetic field produced by the coil at a selected location outside the body |
| $B_m$ | Magnetic field produced by the magnet inside the capsule when the capsule is at any position |
| $\alpha_1$ | Constant factor relating $B_1$ to the coil current |
| $\alpha_2$ | Constant factor relating $B_2$ to the coil current |
| k | Constant ratio relating $\alpha_1$ to $\alpha_2$; a declining factor for going from $B_2$ to $B_1$ |
| $V_1$ unadjusted | Voltage signal produced by sensor 70 inside the capsule when the capsule is at any position |

TABLE 1-continued

Descriptions of the defined variables and constants

| Variable/Constant | Description |
| --- | --- |
| $V_1$ | Portion of $V_1$ unadjusted; represents the magnetic field produced by the coil, NOT necessarily $B_1$ Instance of $V_1$ when the capsule is at the equilibrium position |
| $V_2$ | Voltage signal produced by sensor 72 at the selected location outside the body; represents $B_2$ |
| $V_m$ | Constant signal value representing the magnetic field produced by the magnet and detected by sensor 70 |
| $V_e$ | Error signal sent to the control circuit; represents the capsule deviation from the equilibrium position |

Knowing that $V_1|_{eq}$ and $V_2$ are proportional to $B_1$ and $B_2$ respectively, the following relationship can be developed:

$$k = \frac{B_1}{B_2} = \frac{V_1|_{eq}}{V_2} \quad (7)$$

$$V_2 = \frac{1}{k} V_1 \Big|_{eq} \quad (8)$$

Figure 7:
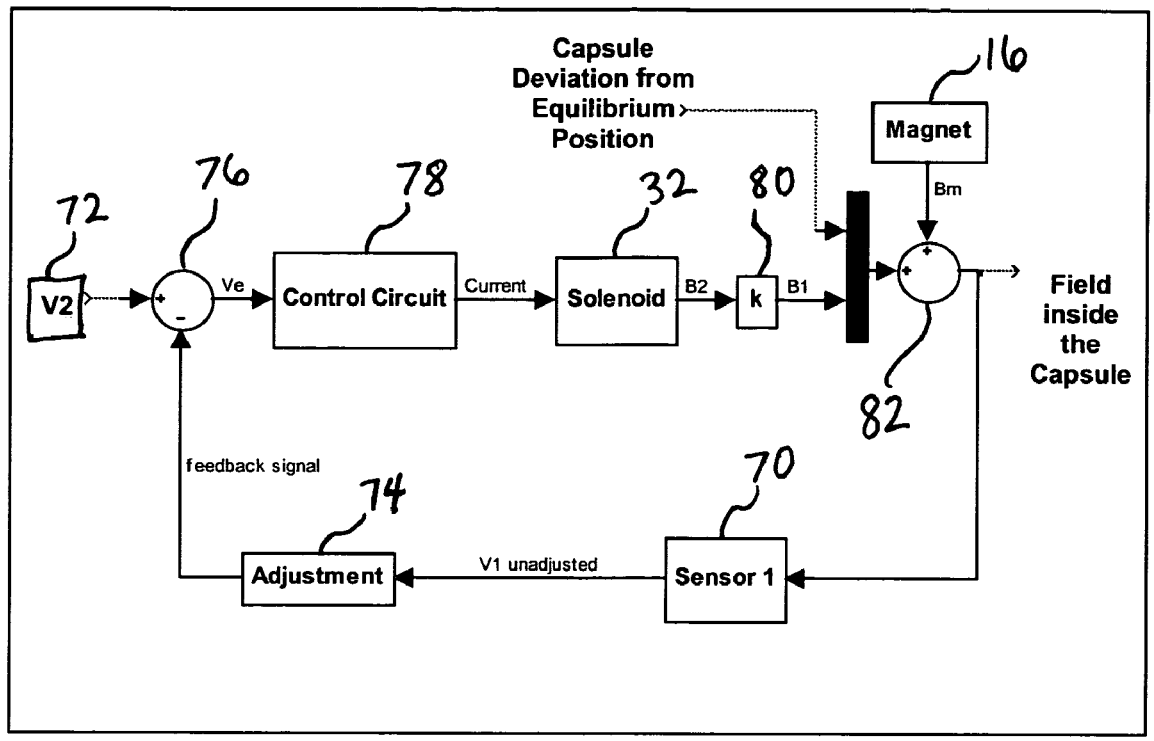
FIG. 7 shows a feedback system for use with an embodiment of the invention.

The purpose of the dual sensor design is to minimize the capsule deviation from the equilibrium position, in such way that the magnetic field inside the capsule approaches ($B_1 + B_m$). In FIG. 7, V1 from sensor 70 is adjusted by subtraction of Vm followed by scaling with the factor in adjustment block 74 to produce a feedback signal. The term $V_1|_{eq} - V_1$ represents the deviation. However, it is a very small signal to deal with. The factor 1/k is applied to amplify the signal. Note that since k is the declining factor 0<k<1, 1/k>1. The term $$\frac{1}{k}(V_1|_{eq} - V_1)$$

still represents the deviation, but amplified. The error signal is then:

$$\frac{1}{k}(V_1|_{eq} - V_1) = \frac{1}{k}V_1\Big|_{eq} - \frac{1}{k}V_1 = V_2 - FeedbackSignal = V_e \quad (9)$$

The feedback signal is subtracted from V2 in block 76 and the result supplied to control circuit 78 as $V_e$. The resulting error signal $V_e$ is an appropriate representation of the deviation. The control circuit 78 makes use of this signal and varies the current supplied to the coil 32. It seems as though there is no fixed target for the control circuit, with the current of the coil constantly being adjusted, leading to a fluctuating $V_2$ signal. However, k (block 80) is the true target for the control system to reach, not $V_2$, because k is the representation of the separation distance between the selected location outside the body and the capsule's equilibrium position. A change in current does not change k, so k is the fixed target for the control system illustrated in FIG. 7. As the capsule 10 deviates in position, this affects the field inside the capsule 10, as illustrated by block 82, producing the field that is measured by sensor 70.

Since the capsule is free to rotate inside the body, the orientation of sensor 70 is a potential problem. If a Hall Effect sensor is used, it is preferred for it to face the coil directly, so that it would detect the magnetic field along the z-axis. The self-orientation of the magnet, a natural phenomenon for aligning its dipole moment with the coil field, is the solution to this problem. If the magnet 16 is physically affixed to the capsule, it would bring the capsule 10, and hence the sensor 70, to face the desired direction. Data from the sensor 70 is communicated to the control system 78 through the transmitter 18. Since the coil 32 will produce a much greater magnetic field, keeping sensor 72 between the coil 32 and the body 36 may not be feasible, considering the limited magnetic range of the sensor 72. Sensor 72 can be placed on the other side of the coil 32, on the centre axis of the coil 32, as shown in FIG. 6. There are two advantages in choosing this location for sensor 72. First, the magnetic field at any point on the centre axis of the coil only has a z-component. Second, the distance between the sensor and the coil can be determined without constraints such as objects being in the way. The distance will be determined by maximizing the use of the magnetic range of the sensor.

In the supine position of the patient 36, and the capsule 10 is being levitated when there is no contraction, the capsule 10 is directly under the electromagnet 52 with the magnetic force equal to the gravitational force. During a contraction when the patient 36 is in the supine position, the capsule 10 (if located in the esophagus) is pushed towards the stomach, until the horizontal component of the magnetic force equals the lateral peristaltic force. The maximum peristaltic force (for the supine position) during a contraction in the worst case is 1.65N. Since the gravitational force (0.108N) is much smaller compared to the peristaltic force, the magnetic force is almost horizontal in order to balance out both forces, meaning that levitation is re-established with the capsule 10 far down the esophagus. When a second electromagnet 54 is introduced on the back side of the patient, the lateral peristaltic force is balanced out by the horizontal components of the magnetic forces. However, the magnetic forces are not symmetrical because of the presence of the gravitational force. Since the peristaltic force varies for every contraction, the strength of the magnetic field produced by the electromagnets 52, 54 is different every time, and the contribution of each electromagnet is different due to the asymmetrical nature of the forces. Controlling the asymmetrical strength of the electromagnets in this situation is more difficult than for the patient in the upright position.

If the patient 36 is positioned upright, the peristaltic force and the gravitational force will be in the same direction. This would allow the magnetic forces to be symmetrical. Levitating the capsule when the patient is in the upright position is similar to the levitation demonstrated in FIG. 3. The same forces act on the capsule 10 as in the case of the supine position, but in different orientation. The electromagnets 32, 34 on both sides of the patient have equal magnetic field strength, simplifying the design of the field control system. The maximum peristaltic force (for the upright position) during a contraction in the worst case is 1.36 N. Combining with the gravitational force, the total maximum vertical force that has to be overcome is (1.36+0.108)=1.47 N, which is less than the maximum supine peristaltic force alone.

In one embodiment the design may use resistive electromagnets made out of copper wire. Even with the additional costs of a power supply with precision regulation and a cooling system, resistive electromagnets are generally much cheaper and simpler to build than superconducting magnets. Soft iron cores are used to concentrate the magnetic field generated. A cylindrical magnet with a diameter of 9.55 mm and a height of 5 mm may be used for levitation. It is larger and heavier than the spherical magnet used in the supine case, but the extra weight is much smaller compared to the peristaltic force. The trade-off of using a larger levitating magnet is the size reduction of the electromagnets required to achieve levitation. The electromagnets are separated into inner and outer coils, similar to those of MRI.

It is desired to use a setup of electromagnets that can produce an upward force of about 1.5 N on the levitating magnet 16 to counter the gravitational and peristaltic forces. The electromagnets will not be running at full capacity most of the time since the duration and frequency of contractions are not high. This means that the current flowing through the coils will be significantly lower when there are no contractions. A design using two coils on either side of the capsule 10 may be used. Each coil 32, 34 has an inner and outer coil, with the inner coils facing each other and between the outer coils. The point of levitation is determined based on the fact that the levitating magnet is most stable just above the inflection point of the magnetic field magnitude. With the origin set at the midpoint between the two pole faces, the inflection point is about to be 150 mm below the origin.

In one embodiment, the cross-sectional areas of the inner and outer coils may be $(90 \times 90) = 8,100$ mm$^2$ and $(120 \times 120) = 14,400$ mm$^2$ respectively (a ratio of 9:16). The current of each inner coil may be 144,000 amp-turns based on trials. To keep things simple, the wire current (in amps) and the wire gauge of the inner and outer coils may be the same. Hence each outer coil has a current of $(144,000 \times 16/9) = 256,000$ amp-turns. The magnitude of magnetic force acting on the levitating magnet is 1.62 N. The force components are as follows: $F_x = -0.229$ N, $F_y = 0.00555$ N, and $F_z = 1.60$ N. The upward force of 1.60 N is enough to guarantee that the capsule will not be lost during a contraction. The small x-component shows that the levitating magnet will be unstable in the x-direction. Feedback control systems and/or diamagnetism can be used for stabilization.

The magnetic field produced by the electromagnets is about 2.1 T at the pole faces of the inner coils, and 0.5 T at the point of levitation. The selection of wire gauge determines the current, power dissipation, mass, and heating rate of an electromagnet. Suitable operating parameters may be obtained from principles applied for the design of MRI magnets.

The concept of using two magnetic sensors 70, 72 can be implemented for the design for the upright position. An additional sensor outside the body 36 may be required because of the introduction of the electromagnets on the back side of the patient. The control circuit 78 may vary the currents of the inner coils only, in which case, since the purpose of the sensors 72 outside the body is to detect the change in magnetic field produced by the electromagnets, the sensors 72 should be closer to the inner coils than to the outer coils. Hence, the sensors 72 should be placed between the body 36 and the electromagnets (at the pole faces of the inner coils). The magnetic field at those locations is substantial and magnetic sensors will not be capable of measuring the field. A magnetic measurement device capable of measuring great field with considerable precision, such as a NMR gaussmeter may be required.

The magnetic field produced by the electromagnets is much smaller when there is no contraction. The currents in the outer coils will decrease significantly after a contraction and will remain at the low level until the next contraction. A contraction can be detected with a pressure sensor mounted at each hemispherical end 20 of the capsule 10. When there is a contraction, the pressure at one end of the capsule increases considerably. Depending on the pressure exerted on the capsule 10, the currents of the outer coils can be increased accordingly to maintain levitation.

For use of the capsule 10 in the colon, additional considerations apply. The maximum peristaltic force is greater in the colon compared to in the esophagus. Colonic pressure activities are complex and variable. They can be categorized into several patterns, with high-amplitude propagated contraction (HAPC) producing the highest peristaltic force. HAPC is not frequent but its duration is relatively long. A study has shown that for a sample of healthy subjects, an average of four HAPCs unrelated to bowel movement, urination, or flatus, occurred in a 24-h period. The average pressure amplitude of a HAPC is 28.7 kPa. The highest average pressure amplitude of non-HAPC colonic activities is only 11.6 kPa, just slightly higher than that of esophageal contractions.

The maximum peristaltic force on the capsule in the colon is ≈4.51 N during a HAPC and ≈1.82 N during other types of colonic contractions. Considering other types of colonic contractions only, the electromagnets will require slight enlargement compared to the design for esophageal use, which is already capable of handling 1.6 N. The size of the electromagnets would have to be increased by at least four times (if not more since the relationship between the size of electromagnets and the force generated is complex and not directly proportional) if the levitation system were designed to handle HAPC in the colon. However, since HAPC does not occur often (roughly once every 6 hours), taking the risk of losing the capsule due to HAPC and starting over again may be a better trade-off compared to the cost of increasing the size of electromagnets significantly. Since the colon has bendings and uneven surface, navigating a capsule within it requires better control and steering than for the esophagus.

In one embodiment, considering the dimensions of the capsule, and a maximal intraluminal pressure of 300 mmHg exerted on it, the magnet-containing capsule can be levitated using an external solenoid with a diameter of about 60 cm, provided that the cylindrical shell of the capsule surrounding the miniature magnet, which is in the shell or part of the shell, is of a strong diamagnetic material, such as bismuth or pyrolytic graphite.

Immaterial modifications may be made to the embodiments disclosed here without departing from the invention.

What is claimed is:

1. Apparatus for monitoring one or more physiological characteristics or parameters in a patient's gastrointestinal tract, comprising:
   a magnetic field generator positioned outside the patient's body for producing a magnetic field inside the person's gastrointestinal tract; and
   a capsule comprising diamagnetic material of sufficient mass to stabilize the capsule in the magnetic field at a desired position in the gastrointestinal tract.

2. The apparatus of claim 1 further comprising at least one physiological sensor carried by the capsule that is capable of sensing a physiological condition or parameter in the gastrointestinal tract.

3. The apparatus of claim 2 further comprising:
   a position sensor configured to produce position signals representing the position of the capsule; and
   the controller being responsive to the position signals to control the position of the capsule in the gastrointestinal tract.

4. The apparatus of claim 3 in which the position sensor is a Hall Effect sensor.

5. The apparatus of claim 4 in which the position sensor is carried by the capsule.

6. The apparatus of claim 5 further comprising a second Hall Effect sensor outside of the body, the controller being responsive to signals from both the Hall Effect sensor in the capsule and the second Hall Effect sensor.

7. The apparatus of claim 1 further comprising:
   a controller having output to the magnetic field generator; and
   the magnetic field generator being responsive to the output from the controller to vary the magnetic field and control the position of the capsule in the gastrointestinal tract.

* * * * *